US007353824B1

(12) United States Patent
Forsyth et al.

(10) Patent No.: US 7,353,824 B1
(45) Date of Patent: Apr. 8, 2008

(54) SELF CONTAINED BREATHING APPARATUS CONTROL SYSTEM FOR ATMOSPHERIC USE

(76) Inventors: David E. Forsyth, 1278 Glenneyre St., Laguna Beach, CA (US) 92651; Wayne K. Miller, 12001 Quartz Valley Rd., Fort Jones, CA (US) 96032

( * ) Notice: Subject to any disclaimer, the term of this patent is extended or adjusted under 35 U.S.C. 154(b) by 0 days.

(21) Appl. No.: 11/091,470

(22) Filed: Mar. 29, 2005

Related U.S. Application Data

(60) Provisional application No. 60/605,561, filed on Aug. 30, 2004.

(51) Int. Cl.
*A61M 16/00* (2006.01)
*A62B 7/00* (2006.01)
*F16K 31/02* (2006.01)

(52) U.S. Cl. .......................... 128/204.22; 128/204.18; 128/204.21; 128/204.23; 128/204.26; 128/200.24

(58) Field of Classification Search ........... 128/204.18, 128/204.21, 204.23, 204.26, 200.24
See application file for complete search history.

(56) References Cited

U.S. PATENT DOCUMENTS 3,923,053 A 12/1975 Jansson
3,957,043 A * 5/1976 Shelby .................. 128/203.14
4,440,166 A 4/1984 Winkler et al.
4,640,277 A 2/1987 Meyer et al.
5,036,841 A 8/1991 Hamilton
5,050,939 A 9/1991 Middelhoven et al.
5,503,145 A * 4/1996 Clough .................. 128/204.22
5,860,418 A 1/1999 Lundberg
6,003,513 A 12/1999 Readey et al.
6,302,106 B1 10/2001 Lewis
6,712,071 B1 3/2004 Parker

* cited by examiner

*Primary Examiner*—Patricia Bianco
*Assistant Examiner*—Nihir Patel
(74) *Attorney, Agent, or Firm*—Dorsey & Whitney LLC

(57) ABSTRACT

An electronic controller having at least one microprocessor controls the solenoid operated valve adding oxygen to the breathing loop of a closed circuit mixed gas rebreather with carbon dioxide scrubbing in maintenance of an oxygen set point in the rage of 0.13-0.50 without any need for monitoring or interpretation of signal data by the operator. The controller receives signals from at least one oxygen sensor located in the breathing loop and sends signals to an indicator: visual, aural, or tactile; during operation providing only intuitively understood normal functioning, limited time remaining, and bail out indications. Automatic diagnosis including oxygen sensor calibration, indication of actions required such as scrubber replacement, and confirmation of an action taken with signals from an action sensor are provided.

28 Claims, 3 Drawing Sheets

SELF CONTAINED BREATHING APPARATUS CONTROL SYSTEM FOR ATMOSPHERIC USE

BENEFIT OF EARLIER FILING DATE

This application claim benefit of the earlier filing date of Provisional Application No. 60/605,561 filed Aug. 30, 2004 in the names of the present applicants.

BACKGROUND OF THE INVENTION

1. Field of the Invention

The present invention relates: generally to respiratory systems supplying respiratory gas to users in hazardous atmospheres; more specifically to electric control means for the supply of respiratory gas to users in hazardous atmospheres; and most particularly to electric control means for the supply of respiratory gas to users in hazardous atmospheres by a respiratory system utilizing means for sensing partial pressure of a gas constituent.

2. General Background

Open circuit breathing systems utilize a compressed gas cylinder and a demand or continuous flow regulator to supply respiratory gas to the operator for inhalation. The exhaled gas is expelled to the ambient atmosphere.

Rebreather based breathing systems utilize the exhaled gas and recycle the unused oxygen contained in the operator's exhalation by means of a breathing loop. The carbon dioxide gas exhaled by the operator is removed by a chemical filter: a carbon dioxide scrubber. Rebreathers are classified into two major groups: semi-closed and fully closed.

Semi-Closed Rebreathers (SCR) are mechanical systems that expel a portion of the gas in the breathing loop at regular intervals. SCR systems are supplied by a premixed hyperoxic gas mixture or, less frequently, by a pure oxygen cylinder and a pure air cylinder. SCR systems are most often used in underwater environments as opposed to atmospheric, because use above land requires near normoxic respiratory gas and consequently high flow rates for the same.

Closed Circuit Rebreathers (CCR) are classified into either mechanical or electronically controlled. Mechanical systems rely on valves and actuating levers with the oldest and simplest closed circuit systems being pure oxygen. Electronic systems are able to maintain a desired level of oxygen in the breathing loop from a pure oxygen supply. In electronically controlled 'mixed gas' rebreathers the oxygen is added or 'mixed' with diluent gas such as air or helium. Whether mechanical or electronic a CCR system completely recycles all expired gas and replenishes the oxygen consumed by the operator. This replenishment is accomplished via purely mechanical means or via electronic and mechanical means. CCR systems provide maximum efficiency in oxygen usage and hence the longest operational time for a given cylinder volume.

Pure oxygen CCR systems are used in shallow water operations as well as land based operation, but are undesirable where:

a. pure oxygen could react with the environment, b. long exposure times are required by the operator, c. underwater depth exceeds 22 feet;

because of, respectively: the risk of rapid combustion, i.e. explosion; immediate and long term oxygen toxicity to human tissues at levels of oxygen above 0.5 atmospheres absolute (ATA); government regulations regarding oxygen toxicity.

Mechanically controlled mixed gas CCR systems are most typically controlled manually by the operator who is then responsible for maintaining the correct oxygen level at all times. These systems require the utmost attention by the operator to ensure that the oxygen level is correct and appropriate for the operator at all times. This requirement renders mechanically controlled manual CCR systems unsatisfactory for use by operators such as fire fighters and emergency first responders who are preoccupied by other continuously urgent tasks during operation.

Electronic or electrically controlled CCR systems monitor the oxygen levels in the breathing loop, via electrochemical oxygen fuel cells and an electronic controller, and maintain a desired oxygen level for the operator in the breathing loop by controlling a solenoid operated valve adding oxygen when open.

Mixed gas closed circuit rebreathers, mechanical or electronic, are supplied by two cylinders of compressed gas, one pure oxygen, the other pure air. The oxygen supply is used to replenish the oxygen consumed by the operator while the air supply is used to dilute the breathing mixture and to provide an emergency or bail out breathing gas supply.

Mixed gas closed circuit rebreathers are complicated and highly technical systems that require the operator to monitor feedback systems and critical processes for failure. The operator must have a high degree of training and use this type of device regularly in order to be proficient not only in the correct operation but also to be able to manage failure modes. Failure modes on mixed gas CCR systems are usually determined by information, or lack thereof, presented to the user on either primary and or secondary displays. In addition, the user must calibrate the system periodically for proper operation. Proper calibration, particularly, is critical to satisfactory operation of a mixed gas CCR system and requires very different tools and operating modes than those required in use of the system.

3. Discussion of the Prior Art

U.S. Pat. No. 5,050,939 issued to Clough discloses an underwater closed circuit mixed gas rebreather with three CPUs: the primary controls the solenoid; the secondary provides the display data and is a back up for solenoid control; while the third CPU is a data display back up that can indicate it is time to manually valve supply gas from a third cylinder that is a back up to the two cylinder main system. Back ups for the solenoid control and data display are provided, with three CPUs, and an emergency cylinder is added, but no provision is made for faulty sensors and the system relies wholly on redundancy in a cascading progression. A high level of technical training is required to operate the system.

U.S. Pat. No. 5,860,418 issued to Lundberg discloses an open circuit breathing system that measures variance of at least one 'functional or status variable' from a 'control value' with at least one sensor and a CPU whereby "the control circuit is activated . . . when there is a significant difference between these values." (Col. 2, lines 10-15) As an alternative "the control circuit is activated manually, by pressing a start button, for instance." (Col. 2, lines 21-23) No provision is made for faulty sensors and system redundancy is not suggested.

U.S. Pat. No. 6,003,513 issued to Readey et al. discloses a closed circuit rebreather with a partial pressure oxygen sensor in the counterlung used to control a valve from a cylinder with a CPU and a stepper motor. U.S. Pat. No.

6,302,106 issued to Lewis discloses a semi-closed circuit rebreather having both gas flows algorithmically controlled in accordance with depth to attain optimum partial oxygen pressure with the diminution of diluent gas at greater pressures being desired to avoid concentration in the blood stream. Neither the problem of faulty sensors nor the need for failsafe systems is addressed.

U.S. Pat. No. 6,712,071 issued to Parker discloses a mixed gas closed circuit rebreather with two independent sets of circuitry that 'are interconnected in a primary and secondary relationship': solenoid operation and display. Both sets of circuitry can perform either operation but the other must be switched manually in the event of power failure in the primary. A back up for the solenoid and the display is thus obtained. Parker is concerned with faulty partial pressure sensors and discloses use of three oxygen partial pressure sensors with rejection of a divergent value: "the signal from the sensor which differs from the each of the other two by the greatest amount is ignored" (col. 3, lines 58-60). Parker is also specific to oxygen levels greater than 0.50 for underwater use and requires a high level of technical training to operate.

Open, semi-closed circuit, and mechanical pure oxygen breathing systems are known dedicated to above land use in low oxygen, toxic, or otherwise hostile atmospheric conditions typically encountered in fire fighting and other emergency situations. U.S. Pat. No. 3,923,053 issued to Jansson utilizes a 'unique scrubber apparatus' suited to the semi-closed circuit rebreather utilizing two alternately filled, vented, and exhausted breathing bags to provide a gradual exhaustion of oxygen rather than the gradual increase obtained with a single cylinder of oxygen and a breathing bag characterizing previous semi-closed circuit breathers. There is no electronic controller and hence no sensing or monitoring capability.

U.S. Pat. No. 4,440,166 issued to Winkler et al. discloses a fail safe for power loss to the solenoid in an 'Electrically and Mechanically Controllable Closed Circuit Respirator' which has a spring loaded piston valve in a medium pressure chamber biased to open an alternative gas supply line upon loss of pressure owing to failure of the solenoid or the electrical system. 'Oxygen sensing means', in the breathing bag, and 'electric control means', for the solenoid, are specified without further detail. Switching to manual control, however, is indicated by a rise in pressure seen in a pneumatic pressure gauge and there is no suggestion of an electronic controller and it is presented as a pure oxygen rebreather only.

U.S. Pat. No. 4,640,277 issued to Meyer et al. discloses "a feedback mechanism responsive to facepiece pressure which actuates a supplemental second inlet air flow path to the facepiece during periods of high user demand" (Abstract) which utilizes a "novel expiration regulator system": "an expiration valve spring controlled to hydraulically open to a first extent in direct response to positive face-piece pressures", indicating a land use open circuit system, that further triggers a solenoid, or "electro assist mechanism which opens the expiration valve to a second and greater extent to reduce facepiece pressure"; or "a novel nonlinear spring mechanism" (col. 3, lines 1-31).

U.S. Pat. No. 5,036,841 issued to Hamilton discloses a "closed circuit breathing apparatus for supplying breathable air to a facepiece of a semi-closed circuit rebreathing system to be worn by a user while working in an irrespirable atmosphere" using a carbon dioxide scrubber, rebreather bag, and a "motorized fan . . . for continuously pumping air" (Abstract) which is 'enriched', i.e. slightly hyperoxic, with the oxygen above 20% and preferably about 30%.

SUMMARY OF PRIOR ART & STATEMENT OF NEED

The prior art discloses provision of redundancy for nearly every rebreathing system and component including electronic controller, control of the solenoid operated valve for oxygen supply, and display of data by an electronic controller for mixed-gas closed circuit rebreathers: e.g. Clough and Parker; but these systems are specific to submerged, mixed gas, closed circuit rebreathers which must supply hyperoxic gas to avoid nitrogen accumulation in the body under elevated pressures. Atmospheric respirators, in contrast, are either open circuit, e.g. Lundberg, or semi-closed circuit, e.g. Jansson.

A large difference is observed between breathing systems used above land and closed circuit rebreathers used in deep water. Mixed gas closed circuit rebreathers utilizing two cylinders, an electronic controller, partial pressure oxygen sensors, and monitors for sensed data in addition to carbon dioxide scrubbing and a solenoid operated valve for oxygen addition are well known for submerged use but are simply unknown for atmospheric use. The fact that semi-closed circuit breathers for atmospheric use are termed closed circuit rebreathers because carbon dioxide scrubbing is utilized and some exhaled gas is recycled indicates the prevalence of open circuit breathers above land rather than use of true closed circuit rebreathers as known for submerged use.

The reason for this, moreover, is readily apparent. No one above ground needs to monitor their depth below surface, decompression illness is not a concern, and fire fighters or other emergency 'first responders' generally do not have the time or training to monitor oxygen levels or other data vital to underwater usage. The complexity of an electronic controller, oxygen and pressure sensors, and data monitor is an effective deterrent to use by fire fighters and other first responders above ground. Operation alone, regardless of maintenance, is prohibitively complicated because of all the information that must be monitored.

Manual overrides of the solenoid valve, or manual valving for an auxiliary gas supply line, are well known and available in rebreathing systems to compensate for the possibility of various system failures. Electronically controlled mixed gas rebreathers can also provide information on monitors interpreted by the operator as indicating that manual intervention is required. The necessary level of operator attention and expertise required in event of a system failure renders these rebreathers impractical for land based environments.

Pure oxygen rebreathers are available for land use, have similar duration characteristics to mixed gas rebreathers, and are mechanically simple systems although significantly more training is required than for open circuit systems for safe use. Pure oxygen systems also pose short and long term oxygen toxicity hazards to the operator and are not acceptable for many situations due to safety issues related to the pure oxygen content of the breathing loop.

Semi-closed circuit rebreathers are not found in land based systems largely because the efficiency in gas supply usage when operating at near normoxic levels is not significantly better than the open circuit systems and the complexity is vastly increased.

The complexities of closed circuit mixed gas rebreathers known for submerged use are, in brief, unnecessary and undesirable in atmospheric use. As a result, and in order to assure sufficient oxygen supply to the user above ground, excessive amounts of normoxic supply gas, typically pure air, characterize above ground breathers or respirators. The inefficiency of this approach limits the operation time available. Alternatively, prolonged use of hyperoxic supply gas, especially pure oxygen, to counter the inefficiency of open or semi-closed breathers, is damaging to the operator and presents the danger of venting excess oxygen in a hazardous environment, an invitation to combustion at precisely the last location desired: inside the mask worn on the user's face.

Submerged use mixed gas closed circuit rebreathers, as opposed to atmospheric respirators, must supply an oxygen content that is variable and capable of achieving at least 70% in order to avoid decompression illness. Atmospheric breathing systems are typically supplied with air, restricting the time available for operation, but avoiding the hazards associated with gas supplies of greater than 50% oxygen. The complexities of mixed gas closed circuit rebreathers, including the need for calibration and for monitoring oxygen levels during operation, is prohibitive to the atmospheric user. The high degree of training and operator attention required, just for monitoring failure modes, is unsatisfactory for operators fighting fires or responding to other emergencies.

Because of the dangers imposed by use of hyperoxic respiratory gas provided by a pure oxygen rebreather and the complexities and attention required of a mixed gas closed circuit rebreather, pure air open circuit breathing systems are indicated for most hazardous atmospheric operations. This, however, imposes severe limits upon operation duration available. The respiratory gas supply must be carried by the operator who is essentially given the choice of limited operation time or a hazardous gas supply as mixed gas closed circuit rebreathing systems are too complicated and require too much attention for use by fire fighters and other emergency first responders. A poignant need is hence discerned for a rebreather control system that is capable of providing sufficient near normoxic respiratory supply gas to operators in hazardous atmospheric environments that does not require special training for maintenance or operation and does not, most of all, require monitoring by the operator during use to ensure proper functioning.

SUMMARY OF THE INVENTION

Objects of the Invention

The encompassing object of the present invention is a respiratory control system for providing sufficient near normoxic respiratory supply gas.

A first auxiliary object of the present invention is a respiratory control system for a mixed gas closed circuit rebreather providing adequate near normoxic respiratory gas to the user that is practical for use by fire fighters and other first responders.

A second auxiliary object of the present invention is a respiratory control system for a mixed gas closed circuit rebreather providing adequate near normoxic respiratory gas to the user that does not require monitoring of data during operation.

A first ancillary object of the present invention is a rebreather control system for a mixed gas closed circuit rebreather providing adequate near normoxic respiratory gas to the user that minimizes single point system failures.

A second ancillary object of the present invention is a rebreather control system for a mixed gas closed circuit rebreather providing adequate near normoxic respiratory gas to the user that performs automatic diagnosis.

A third ancillary object of the present invention is a rebreather control system for a mixed gas closed circuit rebreather providing adequate near normoxic respiratory gas to the user that facilitates maintenance by untrained personnel.

Other ancillary object of the present invention is a rebreather control system for a mixed gas closed circuit rebreather providing adequate near normoxic respiratory gas to the user which eliminates the need for trained or manual-calibration of oxygen sensors and which provides automatic use of redundant, fail safe, rebreather systems and components inclusive of control circuitry and power supplies.

Principles Relating to the Present Invention

In achievement of the above stated objects it is suggested that a control system for a closed circuit mixed gas rebreather with carbon dioxide scrubbing provide maintenance of a single programmable near normoxic set point, i.e. in the range of 0.13-0.50, in response to sensed oxygen levels in the breathing loop. It is suggested that separate cylinders for oxygen and diluent gas be used whereby oxygen is added with a solenoid operated valve controlled by an electronic controller to replenish the oxygen consumed by the operator in respiration and diluent be automatically added to replenish supply gas volume by conventional mechanical means triggered by collapse of the breathing bag. It is suggested that the control system ensure functionality without any need for interpretation of sensed data on the part of the operator.

It is suggested that simplification of the control system be effected with certain assumptions regarding the physical states that can be sensed by an electronic controller through action sensors sensing physical actions involving rebreather components including gas supplies and the carbon dioxide scrubber. It is suggested that replacement of the canister or other container for this chemical filter be sensed by an action sensor and the electronic controller assume that this indicates that a new filter element has been installed and 100% of the estimated maximum time is now available. A timing circuit can then calculate the time remaining on the scrubber.

With regard to the gas supplies it is assumed by the electronic controller that fresh full cylinders, of oxygen and diluent, are properly connected to the rebreather when it is brought into an active mode for operation. Confirmation of gas supply connection with action sensors: pressure sensors on the gas lines between the manually valved regulator, the solenoid operated valve for oxygen addition, and the mechanically triggered valve for diluent; is suggested enabling the electronic controller to confirm that the gas supply is connected to the rebreather with the direct ability to measure both gas cylinders, if pressure sensor data is available, or with the assumption that both cylinders are full thus enabling the timing circuits to estimate the oxygen supply remaining from the frequency of solenoid operation in addition of oxygen.

It is also suggested that simplification and reduction of the information required for operation be achieved with an electronic controller capable of evaluating the electronic signals from at least one, and preferably three, oxygen sensors and taking appropriate action automatically. With three sensors evaluation of each signal in comparison with the other two is possible in addition to range expectations.

In the simplest example, if only one oxygen sensor is used and the signal fails abruptly it is assumed that the operator is still using the rebreather and oxygen is supplied without interruption by opening the solenoid with a frequency consistent with a heavy work load: i.e. a high rate of respiration.

The data from the oxygen sensors is vital to maintenance of the desired oxygen level by the electronic controller in control of the solenoid operated valve used for addition of oxygen. The control system is designed to assure functionality regardless of sensor condition by evaluation and automatic action in the event of single point system failures. Deviation from normal functioning, either from a programmed range or in comparison with other sensors, is monitored by the electronic controller and appropriate action taken in accordance with a programmed protocol.

Together with automatic diagnosis by the electronic controller verifying system functionality a programmed protocol enables simplification of the information conveyed to an indicator sufficiently to allow use of a single indicator element providing intuitively understood indications: of normal functioning, bail out, and preferably at least one limited time remaining indication other than zero, during operation obviating any need for the user to monitor or interpret sensor data. Limited time remaining indications, and any bail out or zero time remaining indication, reflect the duration of continued rebreather operation anticipated by the electronic controller in accordance with a programmed protocol considering a number of monitored variables including the sensed oxygen level, scrubber exhaustion by either a timing circuit or sensed $CO_2$ level if a $CO_2$ sensor is available, voltage of the power supply, and component functionality including microprocessors and solenoid operated valve and supply gases.

It is suggested that the control system have the capability of providing for failsafe redundancy of components including oxygen sensors, solenoid, microprocessor, indicator and power supply. With regard to the oxygen sensors it is suggested that the redundancy be provided by the programmed protocol followed by a microprocessor in the electronic controller for evaluation of multiple oxygen sensors. The capability of evaluating the electronic signals from three oxygen sensors, rejecting divergent or otherwise invalid signals, and relying upon a programmed protocol based upon assumptions with regard to signal validity and operation requirements ensures operational functionality.

Automatic use of redundant components upon failure of the primary including microprocessors, power supplies, or indicator in the elimination of single points of system failure also facilitates assurance of system functionality without requiring monitoring or interpretation of sensor data by the operator. The information required by an operator is hence greatly simplified and untrained operation facilitated by a control system for the rebreather having all signals derived from sensors received by a microprocessor in the electronic controller programmed in accordance with an evaluation protocol for automatic control of the system thereby enabling provision of only intuitively understood indications relating to operational duration to the user during operation.

Most of the electronic components are very quickly tested for functionality by the electronic controller including the power supplies and any redundant microprocessors. Only automatic calibration of one or more partial pressure sensors for oxygen requires this wait period. Alternatively, calibration of the oxygen sensors can be effected with a 100% oxygen environment in which case sensing of the oxygen supply being open, opening of the solenoid operated valve by the electronic controller, and a wait period for ensuring that the breathing loop is filled with pure oxygen is suggested.

It is suggested that valving of the gas supply cylinders be incorporated into a maintenance protocol, either from closed to open, open to closed, or from closed, to open, and closed again in accordance with an indication from the electronic controller. Opening, closing, and opening the gas supply in particular enables the electronic controller to verify that the critical solenoid valve for oxygen supply is in fact functioning properly. Passage from a first physical state to a second physical state and back to the first physical state for sensing removal and replacement of the $CO_2$ scrubber is also suggested. A wait indication for a minute or less with the breathing loop open, in order to ensure that the gas environment inside the breathing loop has achieved stability with the ambient atmospheric gas composition, i.e. 21% oxygen; before automatically calibrating the oxygen sensors is suggested, specifically with a continuous indication followed by either a simple indication that everything is operative or that an action is required. Alternatively, calibration of the oxygen sensors with pure oxygen and an action required indication relating to the oxygen supply along with a wait indication is suggested.

Fulfillment of the principles relating to the present invention discussed above in preferred embodiment of the same is described in further detail below and a fuller appreciation of the advantages and benefits to be derived from such embodiment may be obtained with a reading of this discussion following the brief description of the drawings attached hereto and the nomenclature utilized in both provided immediately below.

| NOMENCLATURE |
|---|
| 10 closed circuit rebreather |
| 11 breathing loop |
| 12 control system |

-continued

| NOMENCLATURE |
| --- |
| 13 $CO_2$ scrubber |
| 15 oxygen supply |
| 16 pressure sensor |
| 17 oxygen sensor |
| 19 action sensor |
| 20 solenoid operated valve |
| 21 circuitry |
| 22 electronic controller |
| 23 microprocessor |
| 25 diluent gas supply |
| 26 power supply |
| 27 indicator |
| 29 indicator element |
| 30 normal functioning indication |
| 31 bail out indication |
| 32 limited time remaining indication |
| 33 wait indication |
| 35 open gas supply valve indication |
| 36 action required indication |
| 37 replace $CO_2$ scrubber indication |
| 39 $CO_2$ sensor |
| 50 gas supply |
| 51 gas line |
| 52 mechanical valve |
| 53 alarm |
| 55 oxygen supply valve |
| 56 biometric sensor |
| 57 alarm signal |
| 59 radio frequency transmitter |
| 60 redundant solenoid operated valve |
| 61 wireless transmission |
| 62 signal |
| 63 redundant microprocessor |
| 65 diluent gas supply valve |
| 66 redundant power supply |
| 67 redundant indicator |
| 69 visual indicator |
| 70 audio indicator |
| 71 tactile indicator |
| 72 mechanical action sensor |
| 73 optical action sensor |
| 75 electrical induction action sensor |
| 76 replace power supply indication |
| 77 replace electronic controller |
| 79 replace $CO_2$ sensor |
| 90 replace $O_2$ sensors |
| 91 programmed oxygen set point range |
| 92 fractional use remaining indication |
| 93 minutes of use remaining indication |

DETAILED DESCRIPTION OF PREFERRED EMBODIMENT

Figure 1:
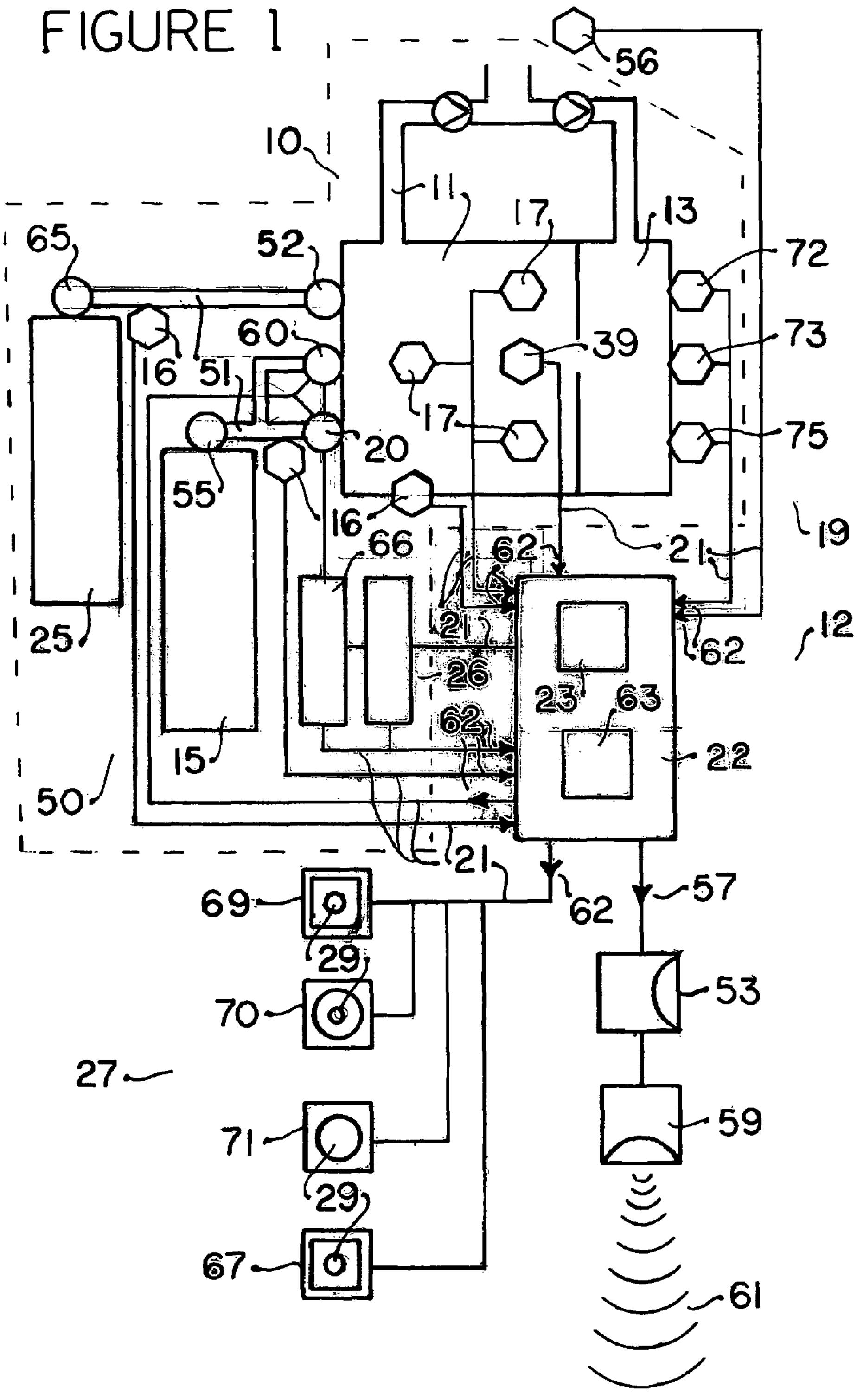
FIG. 1 is a schematic representation of a closed circuit rebreather and control system for the same in preferred accordance with the present invention.
Figure 2:
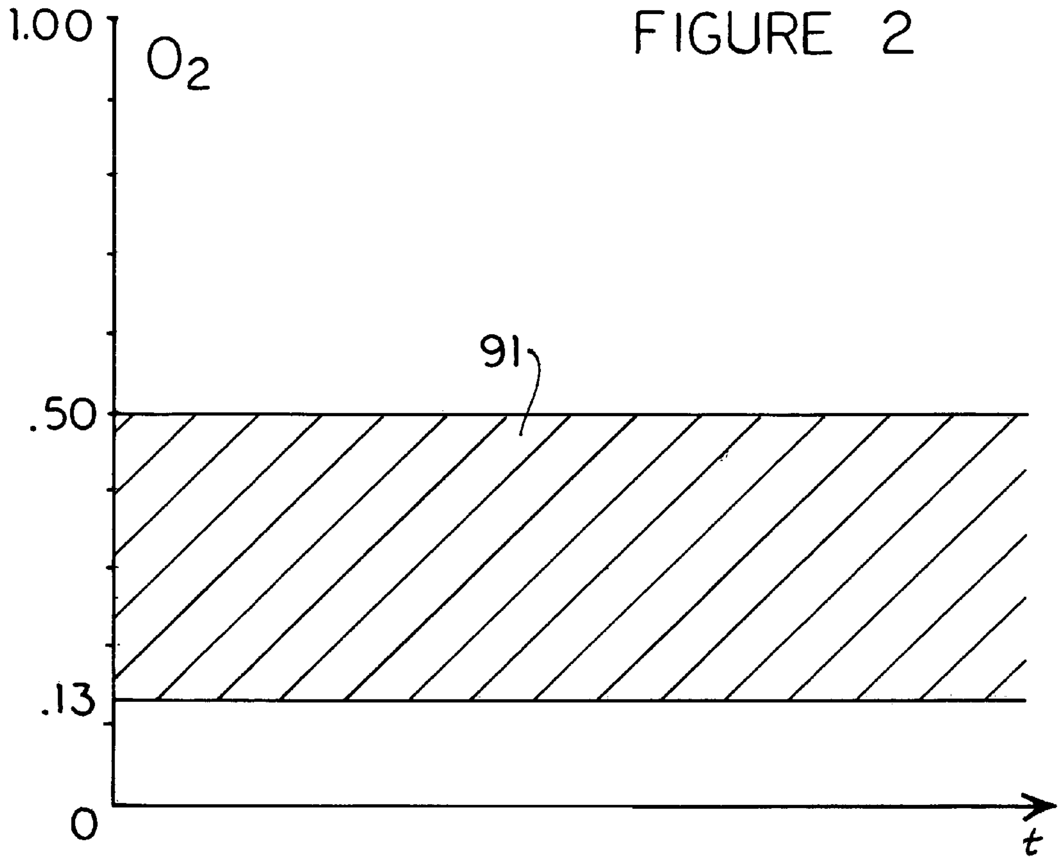
FIG. 2 is a graphic representation of the range of the programmed oxygen set point maintained by a control system in preferred accordance with the present invention.

In preferred embodiment, as seen in FIG. 1, a control system 12 provides for the addition of oxygen through a solenoid operated valve 20 from a gas supply 50 to the breathing loop 11 of a closed circuit rebreather 10 inclusive of a $CO_2$ scrubber 13. The gas supply 50 preferably comprises an oxygen supply 15 and a diluent supply 25 with additions from the latter being made in conventional manner with a mechanical valve 52 operating in response to collapse of the breathing bag. A preferred control system 12 uses an electronic controller 22 possessing at least one microprocessor 23, operably connected to a power supply 26, for the reception of electric signals 62 from at least one oxygen sensor 17 located in the breathing loop 11 and automatic operation of the solenoid operated valve 20, also operably connected to a power supply 26, in maintenance of a single oxygen set point within a programmable oxygen set point range 91, as seen in FIG. 2, of 0.13 to 0.50, providing optimum oxygen content breathing gas to the user in an atmospheric environment without requiring the user, i.e. the operator, to monitor or interpret oxygen sensor 17 or other data.

As seen in FIG. 1, all signals 62 conveying information from any sensor operative upon the closed circuit rebreather 10 inclusive of all oxygen sensors 17 and any pressure sensors 16, action sensors 19, or biometric sensors 56, are preferably received through circuitry 21, i.e. wiring or wireless transmission 61, by the electronic controller 22. And all signals 62 received by the indicator 27 preferably emanate from the electronic controller 22 as do any alarm signals 57 whether sent to a remote location, preferably with a radio frequency transmitter 59, or in generation of a local alarm 53 comprised of any suitable visual or audio means, both visual and audio means, or combined separately or together with remote transmission of an alarm signal 57 via wireless transmission 61.

Figure 3:
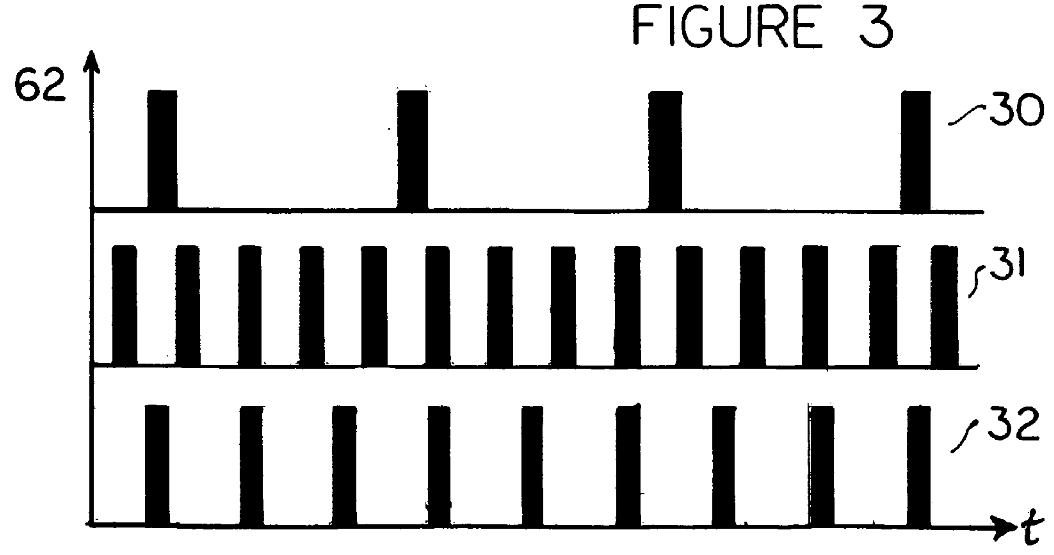
FIG. 3 is a graphic representation of normal functioning, bail out, and limited time remaining indications given in operation in preferred accordance with the present invention.

The control system 12 preferably functions with an indicator 27 having as few as one indicator element 29 permitting use of an audio indicator 70 or a tactile indicator 71 in addition to use of a visual indicator 69 although this is ancillary to the main purpose of reducing and simplifying the information required of the user during operation, preferably to several types of operational indications: a normal functioning indication 30, a bail out indication 31, and at least one limited time remaining indication 32; which preferably reflect, as seen in FIG. 3, alternate states of a signal 62 with a constant frequency that is intuitively understood by an operator: a relatively slow 'blinking' for a normal functioning indication 30; a relatively fast repetition for a bail out indication 31, and a signal 62 yielding an intermediate frequency for a limited time remaining indication 32.

It is emphasized that this is exemplary of the reduction and simplification of the signals 62 received by an indicator 27 from the electronic controller 22 during operation made possible with a control system 12 in preferred accordance with the principles relating to the present invention permitting use of a single indicator element 29 and that even with just a single indicator element 29 intuitively understood indications 30, 31, 32, of normal functioning, bail out, and limited time remaining are readily provided without even variation of signal 62 duration or periods between the same. Alternation of long and short duration signals 62 is also suggested particularly for a limited time remaining indication 32.

It is also noted that the same indications 30, 31, 32 exemplifying those intuitively understood and hence appropriate for operation can be used in a maintenance mode with essentially the same or different significations. It is suggested that the same signal 62 used as a normal functioning indication 30 during operation be used to indicate that a diagnosis mode, preferably including calibration of the oxygen sensors 17, has been completed because the meaning is essentially the same: there is nothing wrong.

Figure 5:
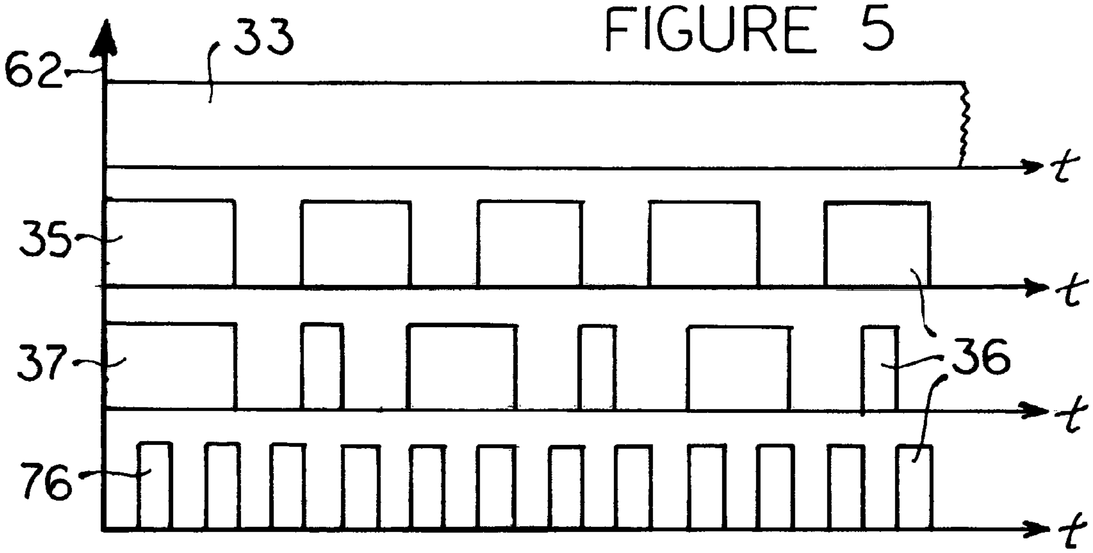
FIG. 5 is a graphic representation of action required indications given in maintenance including wait, open gas supply, replace $CO_2$ scrubber, and replace power supply indications in preferred accordance with the present invention.

It is also suggested, as seen in FIG. 5, that a diagnostic mode have a wait indication 33 of a distinctly different pattern than the signal 62 used to indicate normal functioning 30 or completion of diagnosis, and this distinction is exemplified by a steady 'on' signal 62 state or continuous indication. Similarly, it is considered desirable to distinguish clearly between action required indications 36 and, as further seen in FIG. 5, an exemplary open gas supply valve indication 35 with long duration signals 62 alternating with short durations of absence of the same while an exemplary replace $CO_2$ scrubber indication 37 has two different signal 62 durations alternating with regular absences. The exemplary replace power supply indication 76, in contrast to these two other action required indications 36, is the same as that suggested for the operational bail out indication 31 in FIG. 3.

It is emphasized that more than one indicator element 29 may be utilized and that even with a single indicator element 29 other signal 62 patterns intuitively understood by an untrained operator are readily devised. Increasing frequency of a signal 62 or decreasing lapses between signals 62 intuitively connote urgency as does repetition of signals 62 in series separated by lapses.

And use of a single indicator element 59 enables use of other types of indicators 27 including an audio indicator 70 or a tactile indicator 71 in addition to a visual indicator 69. An audio indicator 70 is audible: it produces sound; while a tactile indicator 71 is felt by the operator but in either case an electromagnet vibrates a membrane with the audio indicator 70 membrane vibrating at a frequency with the range of human hearing, approximately 20-20,000 Hertz, while the tactile indicator 71 membrane preferably operates either below this range or within the lower end of this range hence producing both a vibration that is felt and heard. An audio indicator 70 is hence readily combined with a tactile indicator 71 with one membrane proximate the skin and the other facing outward.

A biometric sensor 56 is also preferably worn by the operator in a position enabling reliable sensing of pulse although the electronic controller 22 which can also use a pressure sensor 16 operative upon an appropriate portion of the breathing loop 11, such as a face mask, for sensing respiration. Alternatively, the electronic controller 22 can track oxygen usage in accordance with the frequency of solenoid operated valve 20 operation in maintaining a set point within the programmed oxygen set point range 91 as this simply replenishes the oxygen used by the operator and hence reflects the rate of respiration of the operator. In brief, a microprocessor 23 possessed by the electronic controller 22 can be programmed to function as a biometric sensor 56 in this manner and an alarm signal 57 produced if the electronic controller 22 senses that the solenoid operated valve 20 hasn't been opened for a period exceeding a predetermined length of time.

The programmed oxygen set point range 91 of 0.13 and 0.50 atmospheres absolute provides for maintenance of a predetermined oxygen level appropriate for atmospheric use at different elevations and for training purposes. At 16,000 feet elevation the normoxic level in absolute atmospheres, because the air is so thin, is only 0.14. At sea level the normoxic level is 0.21. It is typically desired to set the oxygen level to be maintained at an enhanced normoxic level, to err on the side of safety in providing sufficient oxygen, but not to exceed 0.50 in any case because prolonged usage above this level is toxic to human tissue and is potentially inflammable as well. An oxygen level of approximately 0.25-0.35 atmospheres absolute is hence generally recommended with the lower end used at higher elevations. It is also recognized that physical training at lower oxygen levels than normoxic might be used to strengthen the lungs in the fashion that runners will train at higher elevations to increase lung capacity and the lower end of the programmed oxygen set point range 91 of 0.13 and 0.50 atmospheres absolute would be useful for this purpose as well.

In further regard to sensing by the electronic controller 22, particularly in simplification of maintenance and automatic diagnosis, it is first considered that the gas supply 50 preferably comprises both an oxygen supply 15 and a diluent supply 25, and that each is automatically added during operation through a separate gas line 51 by the solenoid operated valve 20 for oxygen and by a mechanical valve 52 triggered by collapse of the breathing bag for diluent. Each gas line 51 is hence pressurized, in contrast to the essentially atmospheric pressure necessarily existing in the breathing loop 11, once the oxygen supply valve 55 and the diluent gas supply valve 65 are opened. Each of these two valves 55, 65 is hence manually operated and the state of each: open or closed; is detectable by a pressure sensor 16 operative upon each respective gas line 51.

Figure 4:
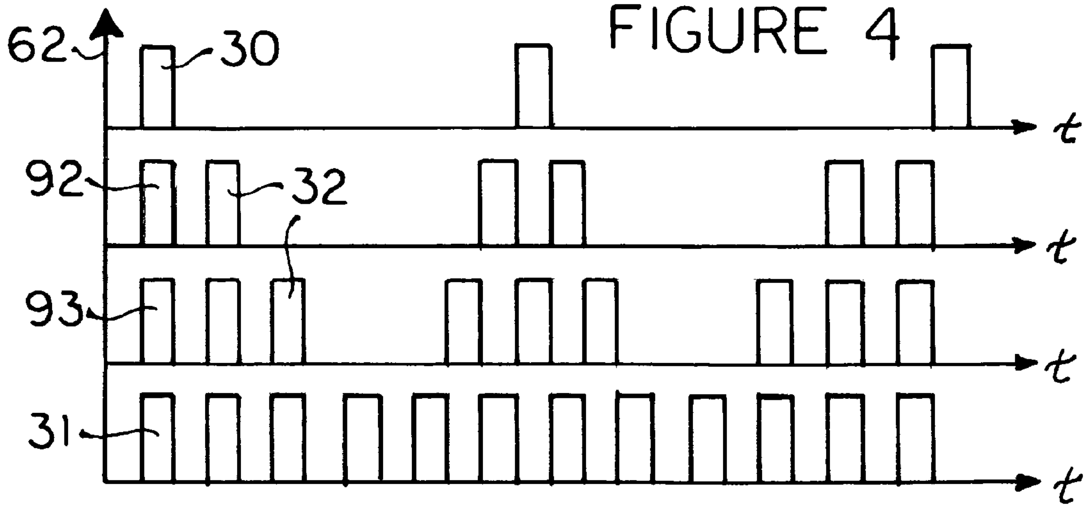
FIG. 4 is a graphic representation of normal functioning, bail out, and two different limited time remaining indications given in operation in preferred accordance with the present invention.

In preferred embodiment a signal 62 from a pressure sensor 16 on both of these gas lines 51 will indicate to the electronic controller 22 that the gas supply 50 is operational and allow the supply pressure to be directly measured enabling the electronic controller 22 to calculate, especially with regard to the amount of oxygen remaining, when to provide a limited time remaining indication 32 as seen in FIGS. 3 & 4. A bail out indication 31, in contrast, will preferably result if the predetermined oxygen level within the programmable oxygen set point range 91 as sensed by the oxygen sensors 17 cannot be maintained despite operation of the solenoid operated valve 20.

A limited time remaining indication 32 as seen in FIGS. 3 & 4, moreover, also preferably results from a calculation by the electronic controller 22 indicating that the $CO_2$ scrubber 13 or oxygen supply 15 is near exhaustion and the first calculation, most easily implemented with a timing circuit, depends upon the assumption that a new $CO_2$ scrubber 13 was installed prior to operation. For this purpose it is preferred that an action sensor 19 operative upon a component necessarily displaced by replacement of the $CO_2$ scrubber 13 be utilized during a maintenance mode and that a replace $CO_2$ scrubber indication 37 as seen in FIG. 5 be generated by the electronic controller 22 during a maintenance mode with the action sensor 19 providing confirmation that the physical action this action required indication 36 identified has been performed.

This confirmation by the electronic controller 22 is made by sensing a change of state in the relevant action sensor 19 from an initial state to another state and back to the initial state whereby the action sensed indicates that the $CO_2$ scrubber 13 has been removed and replaced with opening and closing of the relevant physical component of the closed circuit rebreather 10. The component involved preferably comprises the canister containing the $CO_2$ scrubber 13 or a door or other component requiring opening and closing in replacement of the $CO_2$ scrubber 13. The action sensors 19 preferably comprise simple mechanical action sensors 72, i.e. a simple electrical switch, but other types will certainly suffice including an optical action sensor 73 or an electrical induction action sensor 75 providing a signal 62 that possesses two distinct values, preferably open or closed circuit, in accordance with the state of the physical component concerned.

Figure 6:
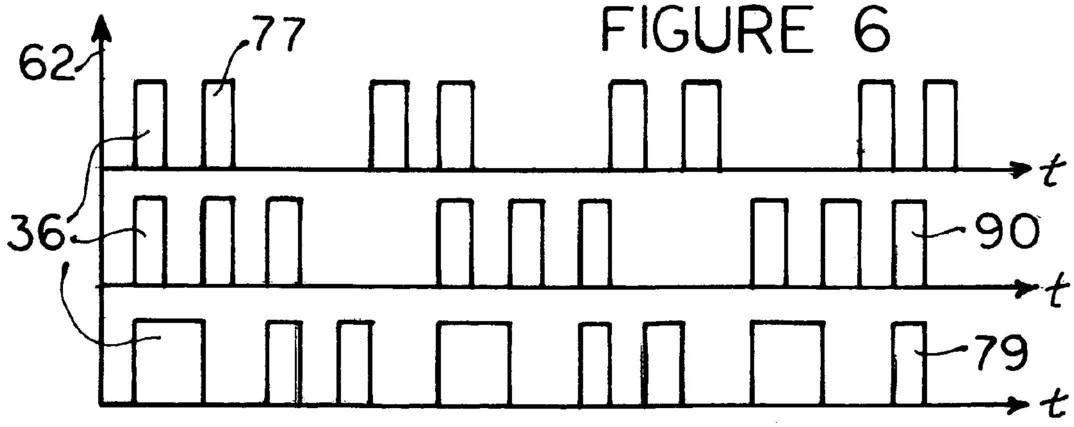
FIG. 6 is a graphic representation of action required indications given in maintenance including replace electronic controller, replace oxygen sensors, and replace $CO_2$ sensor indications in preferred accordance with the present invention.

Other action required indications 36, seen in FIGS. 5 & 6, include a replace power supply indication 76, a replace electronic controller indication 77, a replace $CO_2$ sensor indication 79, and a replace oxygen sensors indication 90. Each comprises a distinct series of alternate signal 62 states varying in duration or frequency and an indicator 27 possessing only a single indicator element 29 can be utilized. It is noted that inclusion of a $CO_2$ sensor 39 operative upon a breathing loop 10 as represented in FIG. 1 will provide actual data to the electronic controller 22 regarding the condition of the $CO_2$ scrubber 13, and hence obviate the need for estimating the time of exhaustion, but that a $CO_2$ sensor 39 is a relatively sophisticated sensor measuring absorption of light in the red end of the spectrum.

Each action required indication 36 can be confirmed with use of an action sensor 19 by the electronic controller 22 but in the case of a new or fresh power supply 26 the state of the same, and any redundant power supply 66, is readily ascertained by an electronic controller 22 having appropriate voltage evaluation circuitry 21. A typical power supply 26, 66 is comprised of a nine volt battery and a typical solenoid in the solenoid operated valve 20 operates down to five volts. As an illustration of the conditions readily sensed by the electronic controller 22 preferably resulting in a limited time remaining indication 32 if the voltage of both batteries typically used as a primary and redundant power supply 26, 66 falls below five volts the solenoid operated valve 20 is expected to cease operation. This condition could be indicated with a bail out indication 31 or anticipated with a limited time remaining indication 32.

It is further noted that if the oxygen level sensed by the electronic controller 22 from the oxygen sensors 17 is still within the programmed oxygen set point range 91, even if the solenoid operated valve 20 has just now failed to operate, then the operator has a number of minutes, approximately five or more but less than ten, of oxygen remaining in the breathing loop 10. The limited time remaining indication 32 preferred in this instance comprises a minutes of use remaining indication 93, which is contrasted with a fractional use remaining indication 92 as both seen in FIG. 4, that would be preferred in anticipation of exhaustion of the power supply 26, oxygen supply 15, or $CO_2$ scrubber 13. In the case of the power supply 26, preferably inclusive of a redundant power supply 66, having a full voltage of nine volts, a sensed voltage of approximately seven volts is recommended for triggering a fractional use remaining indication 92 which indicates that a fraction, preferably less than one quarter but greater than the fraction yielding ten minutes, of the full operational duration of the closed circuit rebreather 10 remains to the operator.

It is preferred that the minutes of use remaining indication 93 be initiated in response to a variety of conditions including sensing of:

1 the solenoid being inoperative by sensing the absence of current in circuitry 21 inclusive of the electronic 'driver' in the electronic controller 22 for this component;
2 the oxygen level falling below a predetermined value inclusive of a value below the predetermined, i.e. set, level, i.e. point, in the programmed oxygen set point range 91;
3 the microprocessor 23, and redundant microprocessor 63 if used as recommended in preferred embodiment, failing in a critical degree; and
4 the voltages of the power supply 26, and redundant power supply 66 if used as recommended in preferred embodiment, falling below a critical threshold value especially in relation to operation of the solenoid operated valve 20 and typically five volts.

The difference between the minutes of use remaining indication 93 and the fractional use remaining indication 92 is preferably consistent with the intuitively understood indications represented in FIG. 4 as opposed to the normal functioning, limited time remaining, and bail out indications 30-32 represented in FIG. 3 with the bail out indication 32 actually indicating zero duration time remaining as opposed to indicating that approximately five minutes of closed circuit rebreather 10 operational duration remain.

It is intended that an operational mode can be immediately entered from completion of: a maintenance and diagnosis mode or a 'sleep' mode following completion of a maintenance and diagnosis mode; by manually opening the oxygen supply valve 55 and the diluent supply valve 65 whereby pressure sensors 16 operative upon each gas line 51 between these valves 55, 65 and, respectively, the solenoid operated valve 20 and the mechanical valve 52 for oxygen and diluent addition send a signal 62 to the electronic controller 22. Another action sensor 19, sending a signal 62 in response to a physical action involving the rebreather 10 including the action of placing the closed circuit rebreather 10 on one's person correctly for usage, i.e. donning the rebreather 10, is also suggested.

It is desired to calibrate the oxygen sensors 17 and verify system operation including power supply 26, 66 and operation of the solenoid operated valve 20 prior to use but this can be done during a diagnostic mode prior to storage with a sleep mode wherein power usage is virtually nil. This assumes that the rebreather 10 is not touched during storage and that storage does not exceed several months. Maintenance at regular intervals of storage is also suggested wherein the rebreather 10 is opened, the carbon dioxide scrubber 13 replaced, and system diagnosis performed by the electronic controller 22 preferably with action required indications 36 such as open gas supply valve indication 35, wait indication 33 for calibration of the oxygen sensors 17, replace power supply indication 76 dependent on sensed voltage, replace oxygen sensors 17 dependent on sensed voltage signal 62, replace electronic controller 77 dependent on microprocessor 23 or other critical circuitry 21 failure, and replace $CO_2$ sensor dependent on signal 62 obtained.

It is also emphasized that this maintenance and diagnosis protocol is exemplary of how the electronic controller 22 can be programmed to obtain a control system for a mixed gas closed circuit rebreather 10 intended for operation in potentially toxic, hypoxic or otherwise hazardous atmospheric environments in which a self contained breathing system is desired for prolonged use by operators without the hazards associated with oxygen levels in excess of 0.50 and without need by the operator of monitoring or interpreting data by elimination of single points of system failure during maintenance and diagnosis wherein action required indications 36 and signals 62 from action sensors 19 in confirmation of the performance of the actions can be used to validate assumptions made by the electronic controller 22 and that the same indicator 27 with as few as a single indicator element 29 used to provide intuitively understood indications 30, 31, 32, in operation can be utilized in providing the action required indications 36 recommended in maintenance and diagnostic modes.

The foregoing is intended to provide one practiced in the art with the best known manner of effectuation and operation of a system in preferred embodiment of the principles relating to the present invention and is not to be construed in any manner as restrictive of the scope of said invention or of the rights and privileges conveyed by Letters Patent in protection of the same and for which purpose we claim:

The invention claimed is:

1. A control system for a closed circuit rebreather possessing a breathing loop including a $CO_2$ scrubber and a solenoid operated valve operably connected to a power supply for addition of oxygen from a gas supply, said control system comprising:

an electronic controller possessing at least one microprocessor operably connected to the power supply, an indicator operably connected to said electronic controller for receiving signals therefrom, and at least one oxygen sensor operably disposed within the breathing loop of the closed circuit rebreather operably connected to said electronic controller for providing signals thereto;

said electronic controller being operably connected to said solenoid operated valve of said closed circuit rebreather for automatic control thereof in addition of oxygen from an oxygen supply to said breathing loop in proportions maintaining, in an operation mode, a programmed oxygen set point in the range of 0.13-0.50 in accordance with signals received from said at least one oxygen sensor;

said indicator providing intuitively understood indications in response to signals from said electronic controller in said operation mode relating to expected duration of rebreather use available based upon at least one factor inclusive of: oxygen level, $CO_2$ scrubber usage, power supply condition, and sensed component failure;

whereby operation of the closed circuit rebreather without need for monitoring and interpretation of sensed signal values by the operator is provided; and wherein said electronic controller is programmed to provide at least one signal to said indicator during a maintenance mode resulting in indication of a specific physical action required involving the rebreather.

2. A control system for a closed circuit rebreather possessing a breathing loop including a $CO_2$ scrubber and a solenoid operated valve operably connected to a power supply for addition of oxygen from a gas supply in accordance with claim 1 wherein one said indication of an action required indicates opening of said gas supply.

3. A control system for a closed circuit rebreather possessing a breathing loop including a $CO_2$ scrubber and a solenoid operated valve operably connected to a power supply for addition of oxygen from a gas supply in accordance with claim 1 wherein one said indication of an action required indicates replacement of said power supply.

4. A control system for a closed circuit rebreather possessing a breathing loop including a $CO_2$ scrubber and a solenoid operated valve operably connected to a power supply for addition of oxygen from a gas supply in accordance with claim 1 wherein one said indication of an action required indicates replacement of said $CO_2$ scrubber.

5. A control system for a closed circuit rebreather possessing a breathing loop including a $CO_2$ scrubber and a solenoid operated valve operably connected to a power supply for addition of oxygen from a gas supply in accordance with claim 1 wherein one said indication of an action required indicates replacement of said electronic controller.

6. A control system for a closed circuit rebreather possessing a breathing loop including a $CO_2$ scrubber and a solenoid operated valve operably connected to a power supply for addition of oxygen from a gas supply in accordance with claim 1 wherein one said indication of an action required indicates replacement of said oxygen sensors.

7. A control system for a closed circuit rebreather possessing a breathing loop including a $CO_2$ scrubber and a solenoid operated valve operably connected to a power supply for addition of oxygen from a gas supply in accordance with claim 1 wherein one said indication of an action required indicates replacement of a $CO_2$ sensor.

8. A control system for a closed circuit rebreather possessing a breathing loop including a $CO_2$ scrubber and a solenoid operated valve operably connected to a power supply for addition of oxygen from a gas supply, said control system comprising:

an electronic controller possessing at least one microprocessor operably connected to the power supply, an indicator operably connected to said electronic controller for receiving signals therefrom, and at least one oxygen sensor operably disposed within the breathing loop of the closed circuit rebreather operably connected to said electronic controller for providing signals thereto;

said electronic controller being operably connected to said solenoid operated valve of said closed circuit rebreather for automatic control thereof in addition of oxygen from an oxygen supply to said breathing loop in proportions maintaining, in an operation mode, a programmed oxygen set point in the range of 0.13-0.50 in accordance with signals received from said at least one oxygen sensor;

said indicator providing intuitively understood indications in response to signals from said electronic controller in said operation mode relating to expected duration of rebreather use available based upon at least one factor inclusive of: oxygen level, $CO_2$ scrubber usage, power supply condition, and sensed component failure;

whereby operation of the closed circuit rebreather without need for monitoring and interpretation of sensed signal values by the operator is provided; and wherein the indications given by said indicator in response to signals from said electronic processor are comprised of only two states, on and off, both variable in duration and frequency.

9. A control system for a closed circuit rebreather possessing a breathing loop including a $CO_2$ scrubber and a solenoid operated valve operably connected to a power supply for addition of oxygen from a gas supply in accordance with claim 8 wherein said indicator possesses only one indicator element.

10. A control system for a closed circuit rebreather possessing a breathing loop including a $CO_2$ scrubber and a solenoid operated valve operably connected to a power supply for addition of oxygen from a gas supply in accordance with claim 8 wherein said indicator is a tactile indicator.

11. A control system for a closed circuit rebreather possessing a breathing loop including a $CO_2$ scrubber and a solenoid operated valve operably connected to a power supply for addition of oxygen from a gas supply in accordance with claim 8 wherein said indicator is an audio indicator.

12. A control system for a closed circuit rebreather possessing a breathing loop including a $CO_2$ scrubber and a solenoid operated valve operably connected to a power supply for addition of oxygen from a gas supply in accordance with claim 8 wherein said indicator is a visual indicator.

13. A control system for a closed circuit rebreather possessing a breathing loop including a $CO_2$ scrubber and a solenoid operated valve operably connected to a power supply for addition of oxygen from a gas supply in accordance with claim 8 wherein a slow alternation of said on and off states of said indicator in operation mode comprises a normal functioning indication.

14. A control system for a closed circuit rebreather possessing a breathing loop including a $CO_2$ scrubber and a solenoid operated valve operably connected to a power supply for addition of oxygen from a gas supply in accordance with claim 8 wherein a rapid alternation of said on and off states of said indicator in operation mode comprises a bail out indication.

15. A control system for a closed circuit rebreather possessing a breathing loop including a $CO_2$ scrubber and a solenoid operated valve operably connected to a power supply for addition of oxygen from a gas supply in accordance with claim 8 wherein an alternation of said on and off states of said indicator intermediate to a slow alternation comprising a normal functioning and a rapid alteration comprising a bail out indication in operation mode comprises a limited time remaining indication.

16. A control system for a closed circuit rebreather possessing a breathing loop including a $CO_2$ scrubber and a solenoid operated valve operably connected to a power supply for addition of oxygen from a gas supply in accordance with claim 8 wherein said electronic controller provides a continuous signal to said indicator resulting in a continuous on wait indication while in a diagnostic mode.

17. A control system for a closed circuit rebreather possessing a breathing loop including a $CO_2$ scrubber and a solenoid operated valve operably connected to a power supply for addition of oxygen from a gas supply in accordance with claim 16 wherein a slow alternation of said on and off states of said indicator after a continuous on wait indication in said diagnostic mode signifies completion of diagnosis mode.

18. A control system for a closed circuit rebreather possessing a breathing loop including a $CO_2$ scrubber and a solenoid operated valve operably connected to a power supply for addition of oxygen from a gas supply, said control system comprising:

an electronic controller possessing at least one microprocessor operably connected to the power supply, an indicator operably connected to said electronic controller for receiving signals therefrom, and at least one oxygen sensor operably disposed within the breathing loop of the closed circuit rebreather operably connected to said electronic controller for providing signals thereto;

said electronic controller being operably connected to said solenoid operated valve of said closed circuit rebreather for automatic control thereof in addition of oxygen from an oxygen supply to said breathing loop in proportions maintaining, in an operation mode, a programmed oxygen set point in the range of 0.13-0.50 in accordance with signals received from said at least one oxygen sensor;

said indicator providing intuitively understood indications in response to signals from said electronic controller in said operation mode relating to expected duration of rebreather use available based upon at least one factor inclusive of: oxygen level, $CO_2$ scrubber usage, power supply condition, and sensed component failure;

whereby operation of the closed circuit rebreather without need for monitoring and interpretation of sensed signal values by the operator is provided; and wherein said electronic controller is programmed to interpret a signal from an at least one action sensor changing from one distinctive value to another distinctive value during a maintenance mode as signifying performance of a physical action involving displacement of a component of said rebreather.

19. A control system for a closed circuit rebreather possessing a breathing loop including a $CO_2$ scrubber and a solenoid operated valve operably connected to a power supply for addition of oxygen from a gas supply in accordance with claim 18 wherein at least one said action sensor is mechanically operated.

20. A control system for a closed circuit rebreather possessing a breathing loop including a $CO_2$ scrubber and a solenoid operated valve operably connected to a power supply for addition of oxygen from a gas supply in accordance with claim 18 wherein at least one said action sensor is operated by electrical induction.

21. A control system for a closed circuit rebreather possessing a breathing loop including a $CO_2$ scrubber and a solenoid operated valve operably connected to a power supply for addition of oxygen from a gas supply in accordance with claim 18 wherein at least one said action sensor is optically operated.

22. A control system for a closed circuit rebreather possessing a breathing loop including a $CO_2$ scrubber and a solenoid operated valve operably connected to a power supply for addition of oxygen from a gas supply in accordance with claim 18 wherein at least one said action sensor is electrochemically operated.

23. A control system for a closed circuit rebreather possessing a breathing loop including a $CO_2$ scrubber and a solenoid operated valve operably connected to a power supply for addition of oxygen from a gas supply in accordance with claim 18 wherein said electronic controller is programmed to interpret the signal from one said action sensor changing from one distinctive value to another as signifying that the rebreather has been donned.

24. A control system for a closed circuit rebreather possessing a breathing loop including a $CO_2$ scrubber and a solenoid operated valve operably connected to a power supply for addition of oxygen from a gas supply in accordance with claim 18 wherein said electronic controller is programmed to interpret the signal from one said action sensor changing from one distinctive value to another as signifying that the carbon dioxide scrubber has been replaced.

25. A control system for a closed circuit rebreather possessing a breathing loop including a $CO_2$ scrubber and a solenoid operated valve operably connected to a power supply for addition of oxygen from a gas supply in accordance with claim 18 wherein said electronic controller is programmed to enter operation mode after receiving a signal from one said action sensor indicating that the oxygen supply has been valved open.

26. A control system for a closed circuit rebreather possessing a breathing loop including a $CO_2$ scrubber and a solenoid operated valve operably connected to a power supply for addition of oxygen from a gas supply in accordance with claim 18 wherein said electronic controller is programmed to enter operation mode after receiving signals from two said action sensors.

27. A control system for a closed circuit rebreather possessing a breathing loop including a $CO_2$ scrubber and a solenoid operated valve operably connected to a power supply for addition of oxygen from a gas supply in accordance with claim 18 wherein said electronic controller is programmed to enter operation mode after receiving signals from at least one said action sensor changing from a first distinctive value to a second distinctive value back to a said first distinctive value.

28. A control system for a closed circuit rebreather possessing a breathing loop including a $CO_2$ scrubber and a solenoid operated valve operably connected to a power supply for addition of oxygen from a gas supply in accordance with claim 27 wherein the signals from at least one said action sensor changing from a first distinctive value to a second distinctive value and back to said first distinctive value signifies that said $CO_2$ scrubber has been replaced.

* * * * *